(12) United States Patent
Sahiholnasab et al.

(10) Patent No.: US 9,406,211 B2
(45) Date of Patent: Aug. 2, 2016

(54) WEARABLE POSTURE REGULATION SYSTEM AND METHOD TO REGULATE POSTURE

(71) Applicant: Medical Wearable Solutions Ltd., Vancouver (CA)

(72) Inventors: Vahid Sahiholnasab, Richmond (CA); Hossein Sahiholnasab, Richmond (CA)

(73) Assignee: Medical Wearable Solutions Ltd., Vancouver (CA)

(*) Notice: Subject to any disclaimer, the term of this patent is extended or adjusted under 35 U.S.C. 154(b) by 0 days.

(21) Appl. No.: 14/753,327

(22) Filed: Jun. 29, 2015

(65) Prior Publication Data

US 2016/0140826 A1    May 19, 2016

Related U.S. Application Data

(60) Provisional application No. 62/081,940, filed on Nov. 19, 2014.

(51) Int. Cl.
*G08B 23/00* (2006.01)
*G08B 21/04* (2006.01)
*A61B 5/103* (2006.01)

(52) U.S. Cl.
CPC ............ *G08B 21/0446* (2013.01); *A61B 5/103* (2013.01)

(58) Field of Classification Search
CPC .... G08B 21/00; G08B 21/02; G08B 21/0446; G08B 21/03; G08B 23/00; A63B 2208/02; A63B 2208/0276; A63B 2208/0271; A63B 2225/50; A63B 2225/685; A63B 24/00; A63B 69/0059; A63B 5/103; A63B 5/1071

USPC ............... 340/539.11, 539.23, 573.3, 573.7, 340/539.1; 482/1, 8–9, 148; 600/300–301; 128/573, 782
See application file for complete search history.

(56) References Cited

U.S. PATENT DOCUMENTS

| 3,208,062 A | 9/1965 | Gregory |
|---|---|---|
| 3,953,831 A | 4/1976 | Estrada |

(Continued)

FOREIGN PATENT DOCUMENTS

| CN | 201259582 Y | 6/2009 |
|---|---|---|
| CN | 201281789 Y | 7/2009 |

(Continued)

OTHER PUBLICATIONS

Lee et al., "A New Posture Monitoring System for Preventing Physical Illness of Smartphone Users", The 10$^{th}$ Annual IEEE CCNC—Work-in-Progress, 2013 IEEE, pp. 713-716.

(Continued)

*Primary Examiner* — Hung T Nguyen
(74) *Attorney, Agent, or Firm* — Nixon & Vanderhye P.C.

(57) ABSTRACT

A wearable posture monitoring and feedback system and related method configured to monitor and provide feedback regarding a user's posture while operating and viewing a portable electronic device includes: a wearable frame configured to be fit on or about a head of the user; a sensor mounted on the wearable frame configured to monitor at least a head position of the user; and a transmitter configured to transmit data related to at least the head position wirelessly from the sensor to a receiver on or in the portable electronic device. The system is configured to (1) provide feedback to the user based on the data from the sensor; and (2) send a signal to alter an output provided to the user by the portable electronic device based on the data from the sensor.

7 Claims, 16 Drawing Sheets

(56) References Cited

U.S. PATENT DOCUMENTS

| | | | |
|---|---|---|---|
| 4,272,764 A | 6/1981 | Herr et al. | |
| 5,158,089 A * | 10/1992 | Swezey | A61B 5/1071 340/573.7 |
| 5,425,378 A * | 6/1995 | Swezey | A61B 5/1071 600/587 |
| 6,147,612 A | 11/2000 | Ruan et al. | |
| 6,204,767 B1 | 3/2001 | Sparks | |
| 6,805,403 B2 | 10/2004 | Buch | |
| 7,004,545 B2 | 2/2006 | Miller | |
| 7,026,940 B2 | 4/2006 | Cherubini | |
| 7,301,465 B2 * | 11/2007 | Tengshe | G08B 21/06 340/575 |
| 7,771,318 B2 | 8/2010 | Narayanaswami | |
| 8,022,981 B2 | 9/2011 | Yoo et al. | |
| 8,083,693 B1 | 12/2011 | McKeon et al. | |
| 9,128,521 B2 * | 9/2015 | Chang | A61B 5/0002 |
| 2001/0054963 A1 | 12/2001 | Cheung | |
| 2007/0149360 A1 | 6/2007 | Narayanaswami | |
| 2010/0079508 A1 * | 4/2010 | Hodge | G06F 3/013 345/697 |
| 2011/0001623 A1 | 1/2011 | Kim | |
| 2011/0275939 A1 | 11/2011 | Walsh et al. | |
| 2012/0068515 A1 | 3/2012 | Bogen | |
| 2012/0075483 A1 * | 3/2012 | Paoletti | A61B 5/4561 348/207.1 |
| 2012/0324946 A1 | 12/2012 | Latouf | |
| 2013/0072820 A1 | 3/2013 | Lee | |
| 2013/0104274 A1 | 5/2013 | Zaouk et al. | |
| 2014/0028458 A1 | 1/2014 | Shin et al. | |
| 2014/0309752 A1 * | 10/2014 | Yuzurihara | G05B 15/02 700/13 |

FOREIGN PATENT DOCUMENTS

| | | |
|---|---|---|
| GB | 2179852 | 3/1987 |
| JP | 2008-264188 | 11/2008 |
| WO | WO 2015/007132 | 1/2015 |

OTHER PUBLICATIONS

Jaimes et al., "Sit Straight (and tell me what I did today): A Human Posture Alarm and Activity Summarization System", FXPAL Japan, Corporate Research Group, Fuji Xerox Co., Ltd., Japan, Nov. 11, 2005, pp. 23-34.

Notification of Transmittal of the International Search Report and the Written Opinion of the International Searching Authority, or the Declaration mailed Jan. 26, 2016 (8 pages), International Search Report (4 pages), and Written Opinion of the International Searching Authority (7 pages).

Tanaka et al., "Nekoze! Monitoring and. Detecting Head .Posture while Wotking with Laptop and Mobile Phone", 2015 9th International Conference on Pervasive Computing Technologies for Healthcare (PervasiveHeahh). May 20-23, 2015, Istanbul, Turkey, pp. 237-240.

Hong et al., "Demo Abstract: SEPTIMU Continuous In-situ Human Wellness Monitoring and Feedback using Sensors Embedded in Earphones". IPSN'12, Apr. 16-20, 2012, Beijing, China, pp. 159-160.

Hu et al., "Septimu2: Earphones for Continuous and Non-Intrusive Physiological and a Environmental Monitoring", SeoSys'12 Proceedings of the 10th ACM Conference on Embedded Network Sensor Systems, Nov. 9, 2012, Toronto, Canada, pp. 387-388.

Kim et al., "Detecting and Preventing Forward Head Posture with Wireless Inertial Body Sensor Networks", 201 1 International Conference on Body Sensor Networks, Mar. 23-25, 2011, Dallas, USA, pp. 125-126.

Lee et al., "Mobile Posture Monitoring System to Prevent Physical Health Risk of Smartphooe Users", UbiComp'12, Sep. 5-8, 2012 (Aug. 9, 2014 Pittsburgh, USA,pp. 592-593.

Lopez-Quintana et al., "Accelerometer Array and Method to obtain a 3D Representation of the Spine Posture", 2011 international Conference on Broadband and Wireless Computing, Communication and Applications, Oct. 26-28, 2011, Barcelone. Spain, pp. 466-471.

Lou et al., "Development of a smart garment to reduce kyphosis during daily living", Medical & Biological Engineering & Computing, Nov. 2012, vol. 50, No. 11, pp. 1147-1154, published online Dec. 18, 2011.

Wong et al., "Smart garment for trunk posture nionitoring. A preliminary study", Seoliosis. vol. 3, No. 7, Published: May 20, 2008.

Wong et al., "Trunk posture monitoring vdth inertial sensors", European Spine Journal, May 2008, vol. 17, No. 5, pp. 743-753, Published online: Jan. 15, 2008.

* cited by examiner

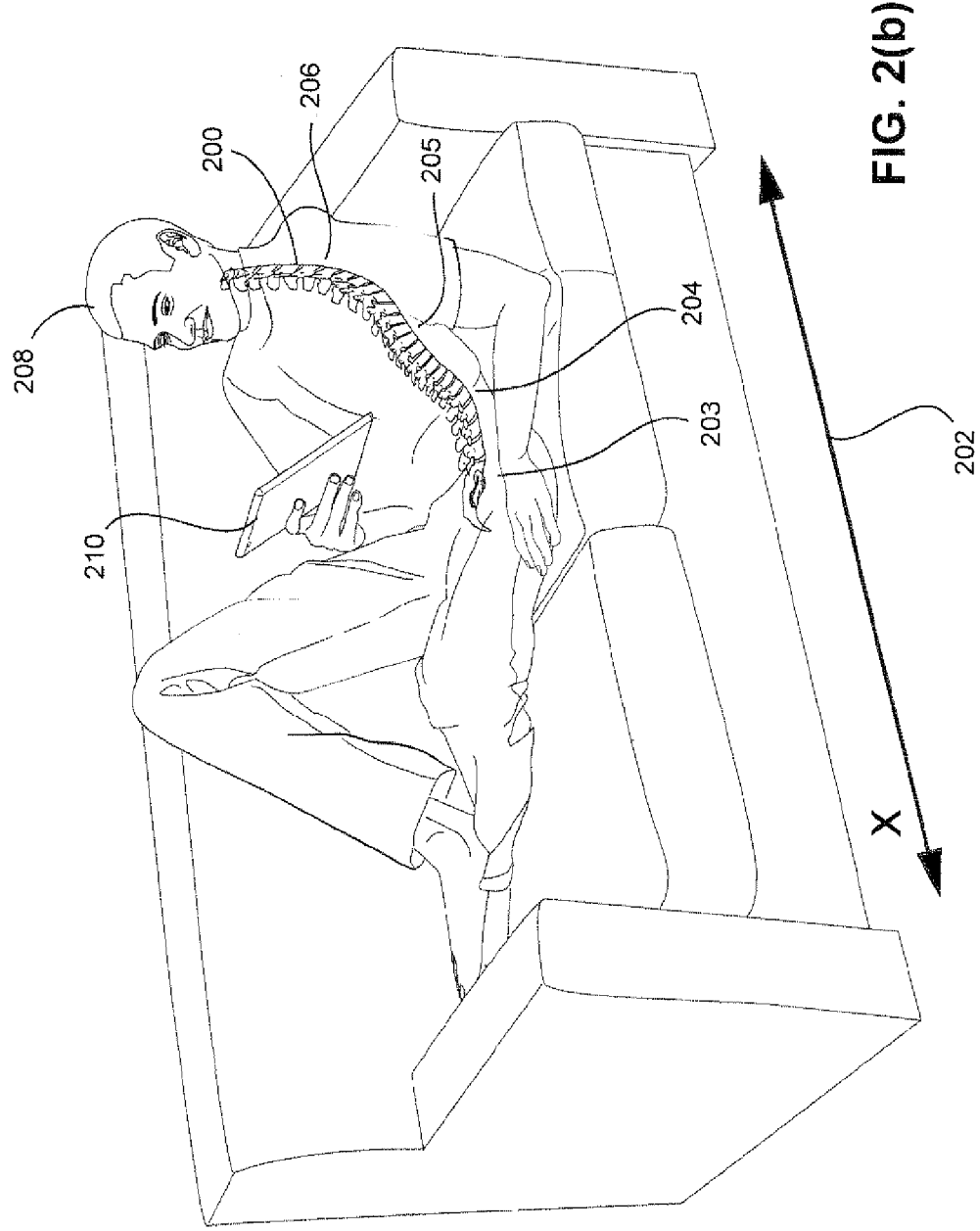

WEARABLE POSTURE REGULATION SYSTEM AND METHOD TO REGULATE POSTURE

CROSS-REFERENCES TO RELATED APPLICATIONS

This application claims priority to U.S. Provisional Application No. 62/081,940, filed Nov. 19, 2014, the entire content of which is hereby incorporated by reference.

FIELD OF THE PRESENT TECHNOLOGY

The present technology relates to a device and method for detecting, preventing, and correcting poor posture while using an electronic device, and in particular a handheld electronic device, alerting a user to said poor posture during use of said electronic device with a variety of warnings, and optionally altering the performance of said electronic device in the event that poor posture continues to be displayed after a predetermined number of warnings have been issued.

The present technology relates to a device for preventing and correcting posture-related ailments resulting from the use of electronic devices, and in particular handheld electronic devices, which encourage users to sit in a position exhibiting poor posture. The present technology specifically relates to providing feedback to a user concerning unhealthy posture during operation of a variety of electronic devices requiring a hand-held component.

BACKGROUND OF THE PRESENT TECHNOLOGY

With the continued advancements in electronic devices providing increasingly engaging displays and programming, large numbers of people are spending extended periods of time using electronic devices. Many of the electronic devices in use today either rely on a hand-held component, e.g., a controller or remote, or the devices themselves are designed to be hand-held during use.

As a result of increased popularity of and access to such electronic devices, health effects associated with prolonged and repeated use of such devices have begun to be observed. In response to observed maladies seemingly related to hand-held electronic devices, such as smartphones and tablets, studies have been conducted that demonstrate users of such devices spend long periods of time in unhealthy postures with their necks (and back) bent forward while staring at and concentrating on a screen.

In particular, the use of electronic devices relying on hand-held components may cause vision problems and encourage users to operate the devices while oriented in a variety of positions which compromise their posture.

In the case of posture problems, cases can present in the form of musculoskeletal abnormalities and dysfunction, along with associated developmental disorders that can occur if the posture problems cause the abnormalities and dysfunction before the user's body has finished growing to maturity.

One such developmental disorder is known as "Gameboy Back," which was first described by a pair of Dutch orthopedic surgeons in Dutch medical journal, "Medische Contact," in its August 2013 issue. Gameboy Back is a medical condition that refers to an abnormal curvature of the spine, particularly in children, who spend their days hunched over game consoles and other handheld devices such as smartphones and tablets. The persons observed exhibited abnormal posture in the form of a C-shaped spine (instead of the normal S-shape) and complained of back and neck pain.

"Gameboy Disease" was first described by Dr. Vahid Sahiholnasab in August 2014. Gameboy Disease has multiple dimensions and involves both the musculoskeletal system and the central nervous system. Deformities associated with Gameboy Disease may interfere with normal body movements and activities. Such deformities can further lead to difficulty exercising, along with related complications associated with overweightness and obesity. Associated psychological effects include depression, loneliness, and lack of self-confidence.

There remains a need to address a growing problem affecting people, and young people in particular, where the growing prevalence of use of electronics having a hand-held component causes the person using the electronic device to sit in a way which is considered poor posture and can have negative health effects both in the immediate and long-term. The damage caused by the poor posture can be especially debilitating to young persons, wherein the poor posture can lead to musculo-skeletal abnormalities and dysfunction and developmental dangers, including but not limited to deformations of the spine and muscles connected to the spine, head, and neck.

There is a need for a device which monitors a user's posture during use of an electronic device with a handheld component and provides feedback in a way that may discourage poor posture and thus prevent the above-discussed medical complications associated with poor posture exhibited during use of said electronic devices.

SUMMARY OF THE PRESENT TECHNOLOGY

In one example of the present technology, a wearable posture monitoring and feedback system configured to monitor and provide feedback regarding a user's posture while operating and viewing a portable electronic device comprises: a wearable frame configured to be fit on or about a head of the user; a sensor mounted on the wearable frame configured to monitor at least a head position of the user; and a transmitter configured to transmit data related to at least the head position wirelessly from the sensor to a receiver on or in the portable electronic device; wherein: the system is configured to (1) provide feedback to the user based on the data from the sensor; and (2) send a signal to alter an output provided to the user by the portable electronic device based on the data from the sensor.

As an additional example, a method for preventing "Gameboy disease" and other posture-related conditions resulting from poor posture during a user's operating and viewing of a portable electronic device comprises: monitoring the posture of the user during use of the portable electronic device; providing feedback to the user concerning posture during use of the portable electronic device; and altering the functionality of the portable electronic device based on the posture of the user; wherein abnormal posture may result in the functionality of the portable electronic device being altered in at least one respect.

It may of course be understood that, while the present technology may be described in connection with several wearable devices, those in this art may recognize that such a description represents one or more examples and is thus non-limiting. Thus, the structural and/or functional features of the present technology may, for example, also be usefully employed in other posture monitoring devices, including video monitoring, other wearable devices, and other methods of monitoring a user during use of a handheld electronic device.

Other aspects, features, and advantages of this technology may become apparent from the following detailed description when taken in conjunction with the accompanying drawings, which are a part of this disclosure and which illustrate, by way of example, principles of this invention. Any examples described or suggested herein may be combined with any other examples.

BRIEF DESCRIPTION OF THE DRAWINGS

The accompanying drawings facilitate an understanding of various examples of this technology. In such drawings:

FIG. 2(b) is an illustration of a person seated in a position between laying prone and sitting up and also exhibiting poor posture.

DETAILED DESCRIPTION OF THE PRESENT TECHNOLOGY

The following includes descriptions of several illustrated examples of the present technology, which may share common characteristics and features. It is to be understood that one or more features of any one example may be combinable with one or more features of any other examples. In addition, each single feature or combination of features in any of the examples may constitute an additional example.

The present technology relates to providing a posture monitoring system which may be wearable during use of an electronic device with a handheld component. The electronic device may be entirely handheld, such as would be the case with a smartphone or a tablet device. The electronic device may also have a handheld component, such as a remote control or a controller such as may accompany console gaming systems. The electronic device may also be a wearable device, such as a watch, e.g., a Smartwatch, which causes a user to look down while operating. Current examples of a Smartwatch include the "Apple Watch" and "Samsung Gear." Other examples include Facebook's Oculus VR, which is a head-mounted display designed to provide immersive virtual reality. The Oculus VR device weighs enough to contribute to a natural tendency for the user to tilt the head downward, partially due to gravity, which may result in poor posture in the long run.

The present technology provides a wearable component which includes sensors for monitoring posture. Sensors provided may include a variety of sensor types, including tilt sensors, proximity sensors, vibration sensors, and other sensors practically useful in determining a user's posture and/or location relative to a handheld electronic device. Other sensors may include an accelerometer, a gyroscope, and/or a magnetometer.

1. Posture

Figure 1:
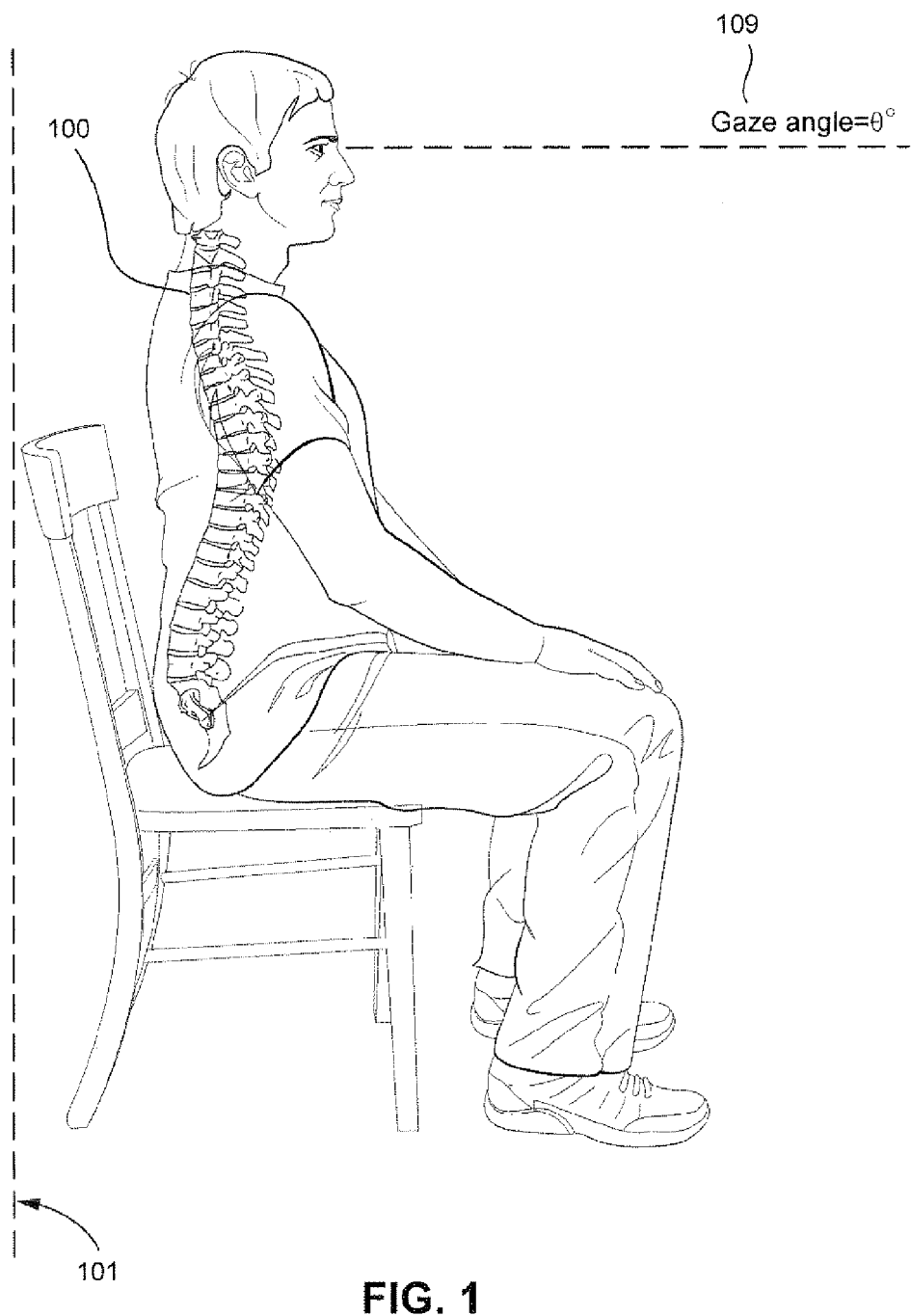
FIG. 1 is an illustration of a person seated and exhibiting proper posture.

FIG. 1 demonstrates exemplary "good" posture for a person in a seated position. As indicated in the figure, posture is considered good when the spine of a person is positioned correctly, e.g., when the spine exhibits a roughly S-shaped curvature. Spine 100 is naturally S-shaped, but in aggregate mirrors vertical plane 101. As can be seen in FIG. 1, correct posture involves the head being held above the shoulders. In a correct seated posture; the cranium, neck, and spine down through the sacral region substantially line up and run parallel to vertical plane 101. Further, "good" seated posture results in a gaze angle 109 of approximately zero degrees relative to the horizontal. A person can be considered to be exhibiting good posture while viewing an object at between zero and fifteen degrees deviation from the horizontal.

Figure 2A:
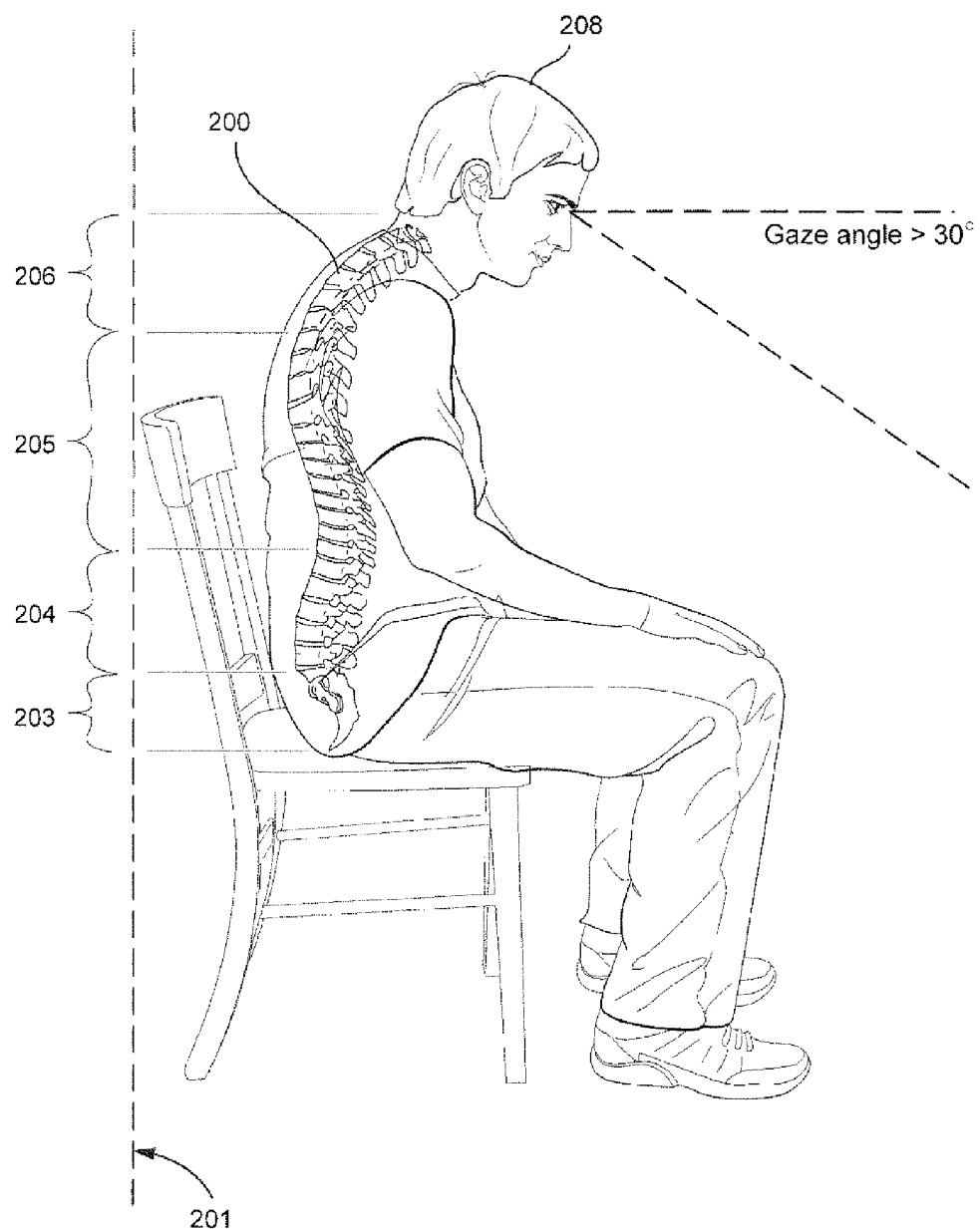
FIG. 2(a) is an illustration of a person seated in a way exhibiting an example of improper posture.

FIGS. 2(a) and 2(b) demonstrate poor posture. FIG. 2(a) demonstrates an example of a seated person exhibiting a C-shaped back. In this example, spine 200 is forced into a C-shape by the person leaning forward. In users of electronic devices with a handheld component, such movement is caused by a person leaning forward to view and interact with the handheld component. Unlike in FIG. 1, the spine in this example fails to substantially align with vertical plane 201 through its length. As illustrated in FIG. 2(a), poor posture related to looking down, e.g., at a handheld electronic device, occurs where the gaze angle exceeds 30 degrees down from the horizontal. The spine can be classified into different sections: the sacral region 203, the lumber region (5 vertebrae) 204, the thoracic region (12 vertebrae) 205, and the cervical region (7 vertebrae) 206. FIG. 2(b) demonstrates an additional example of a person orienting themselves in a way which causes stress to the back, whereby a user of a handheld electronic device slouches or sits on a flat surface such as a floor or couch such that their spine is aligned horizontally, requiring the user to maintain a crunched or partially upright position to see and interact with the electronic device. In this example, spine 200 is oriented partially horizontally, with the lumbar portion 204 and at least some of the thoracic section 205 of the spine substantially aligned with a horizontal plane 202. Simultaneously, since the user is attempting to sit up from this position to view a handheld electronic device, at least a portion of an upper part of the thoracic section 205 of the spine and the cervical section 206 of the spine are curled upwards and bent forward and compressed to position the cranium vertically. This head position, like in FIG. 1, orients the head 208 such that the user can see and interact with the handheld electronic device 210.

2. Head and Neck Involvement with Posture

Figure 3A:
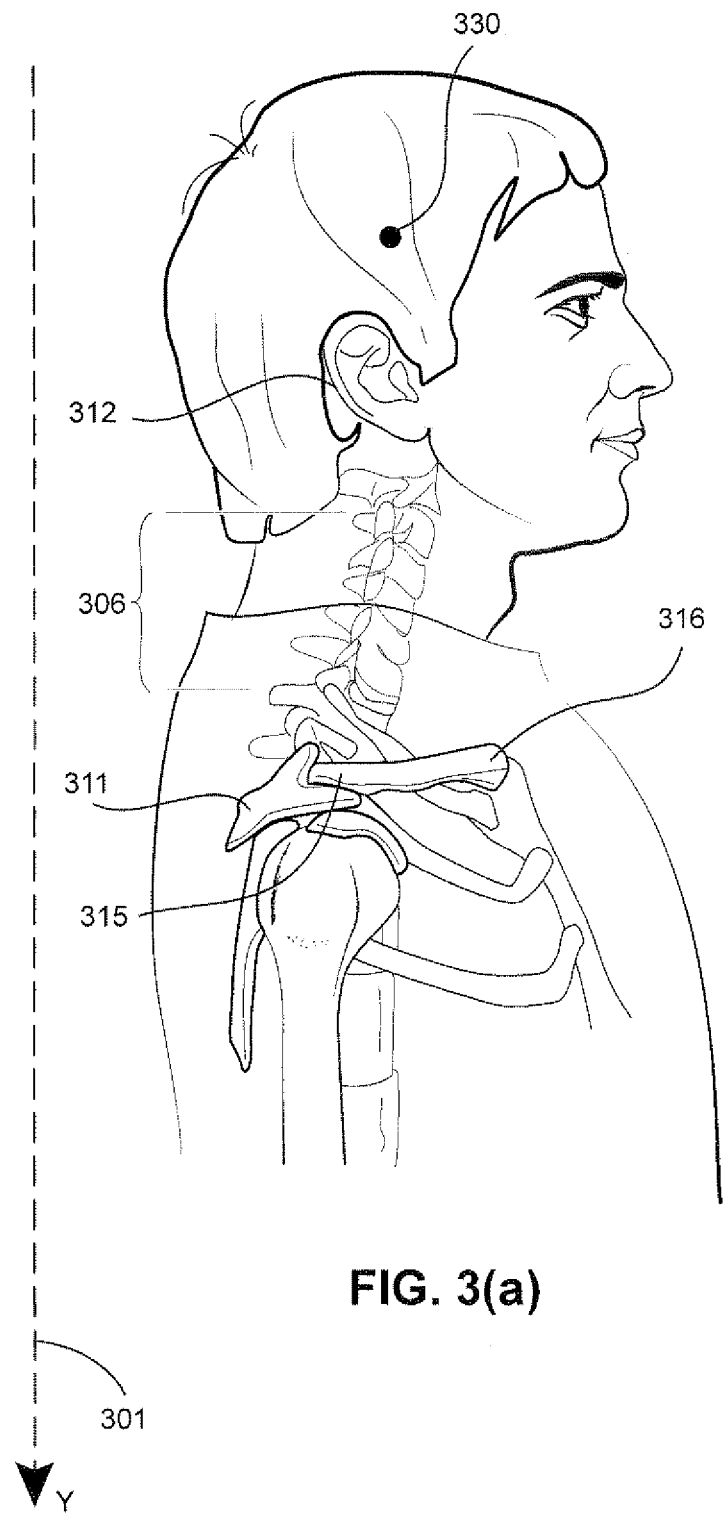
FIG. 3(a) is illustration of head position relative to shoulder position in a correct posture position.
Figure 3B:
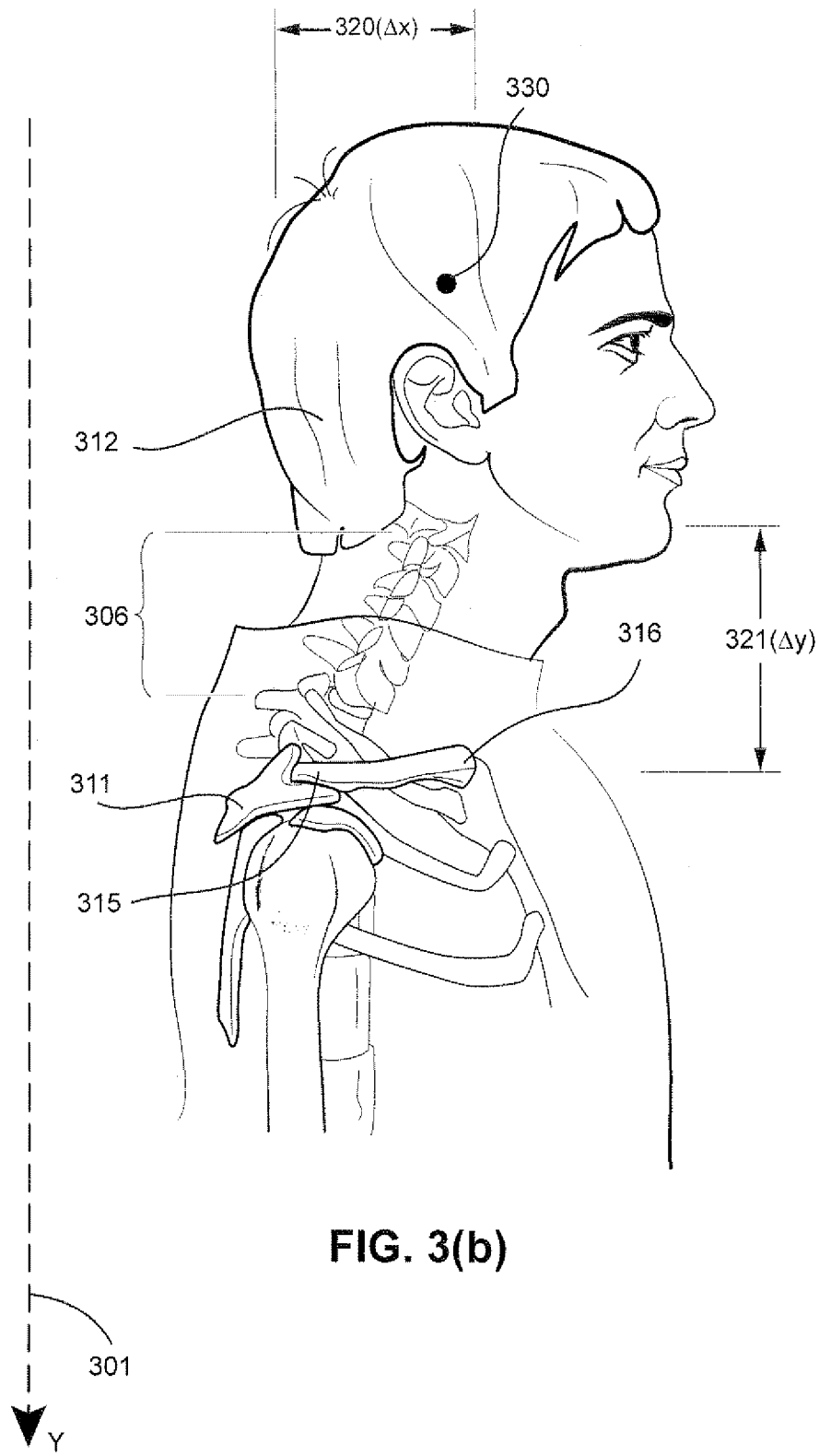
FIG. 3(b) is an illustration of head position relative to shoulder position in a head forward position, which is not correct posture.
Figure 3C:
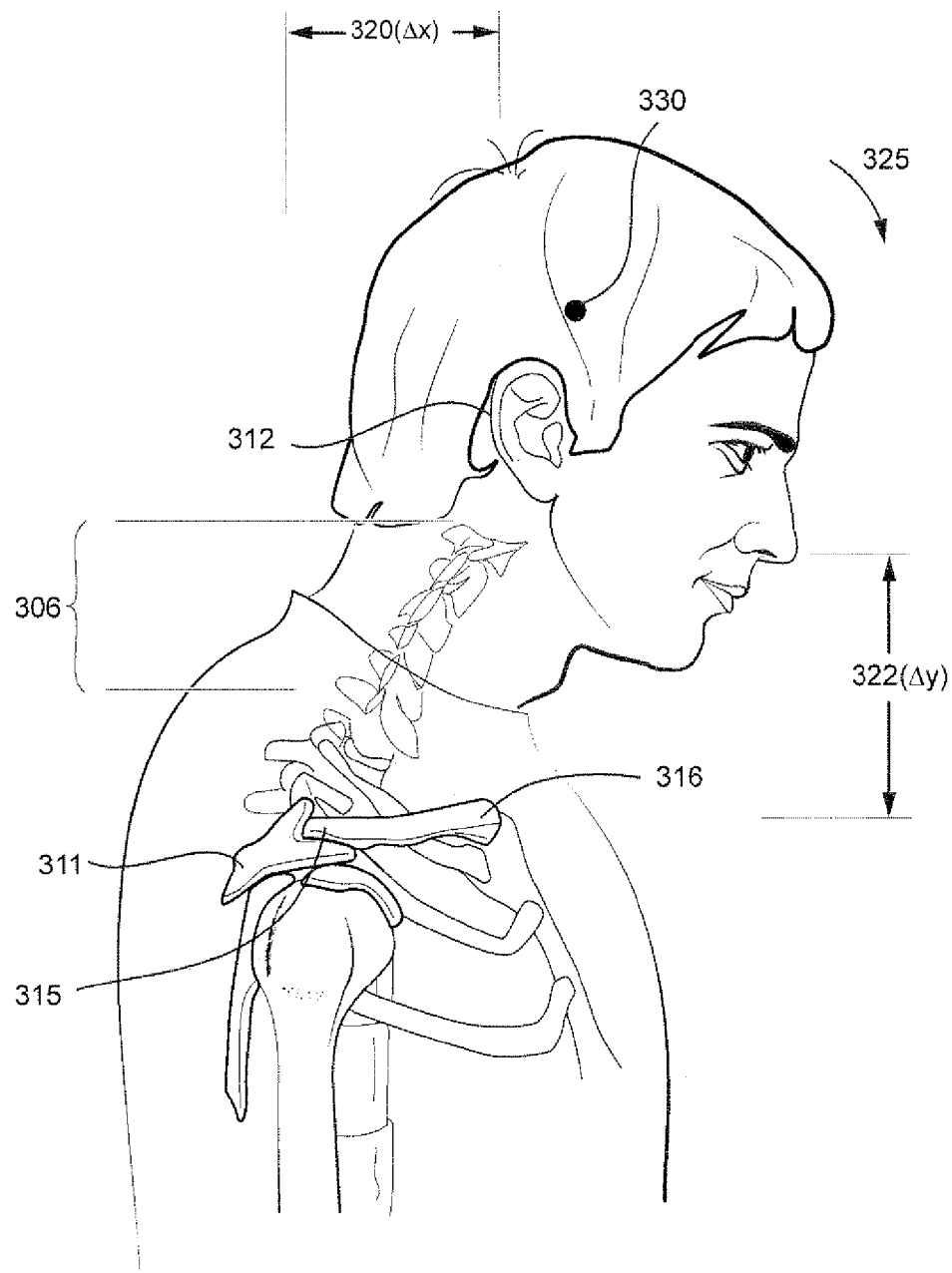
FIG. 3(c) is an illustration of head position relative to shoulder position in a head forward and tilted position, which is not correct posture.

FIGS. 3(a)-3(c) further illustrate good and poor posture with respect to the head and neck relationship. As can be seen in FIG. 3(a), a head in the correct posture position is positioned above the shoulders 311, with minimal strain to the neck muscles and associated connective tissues. If a person is standing properly, a person's shoulders 311, ears 312, hips, knees, and ankles should be stacked above each other, with an imaginary straight line being able to be drawn from the top of the head, through the body's center, and down to the bottom of the feet. Correct head position related to posture can be determined by comparing the lower ear lobe 312 with the acromioclavicular joint 315 (where the collarbone attaches to the shoulder). These two body landmarks should be lined up in a substantially vertical plane 301.

Contrast FIG. 3(a) with FIG. 3(b), where the head is in a forward position denoted as being forward a distance ($\Delta X$) 320 relative to FIG. 3(a), and the ear 312 and collarbone 316 are not aligned vertically. In the orientation illustrated in FIG. 3(b), the neck muscles are strained, the connective tissues are stretched, and the cartilage and bones are compressed due to the increased force caused by the forward head position, denoted as a distance 321 ($\Delta Y$). For instance, based on an average head, the head weighs approximately 12 lbs. in the correct upright position. As the head moves forward, the weight (downward force) of the head increases: two inches of forward head movement increases the weight of the head to approximately 32 lbs. and three inches of forward head movement increases the weight of the head to approximately 42 lbs. of force. That increased weight must be supported by the muscles of the neck and upper back. Additionally, the forward movement of the head shifts its center of gravity 330 forward, causing the upper body to drift backward, the hips to tilt forward, and strain to the middle and lower back as a result. Further, the additional force of forward head positions can cause the bones of the neck to compress their associated cartilage, blood supplies, and nerves.

FIG. 3(c) illustrates a forward head posture whereby a person has also tilted their head downwards to look at a handheld electronic device. Postural issues associate with forward head position issues are compounded by the user additionally looking down at the device, causing angular head tilt 325 in addition to the forward lateral movement 320 associated generally with forward head resulting from poor posture. Thus, the forward lateral movement 320 in conjunction with the head tilt 325 further moves the head's center of gravity 330. The tilt 325 further compresses the bones, muscles, etc. (denoted as a distance ($\Delta Y$) 322), and compounds issues with pinched nerves and cartilage discs. Prolonged use of handheld devices while exhibiting this improper posture can result in permanent spinal and muscle deformities.

3. Posture Monitoring System

Figure 4A:
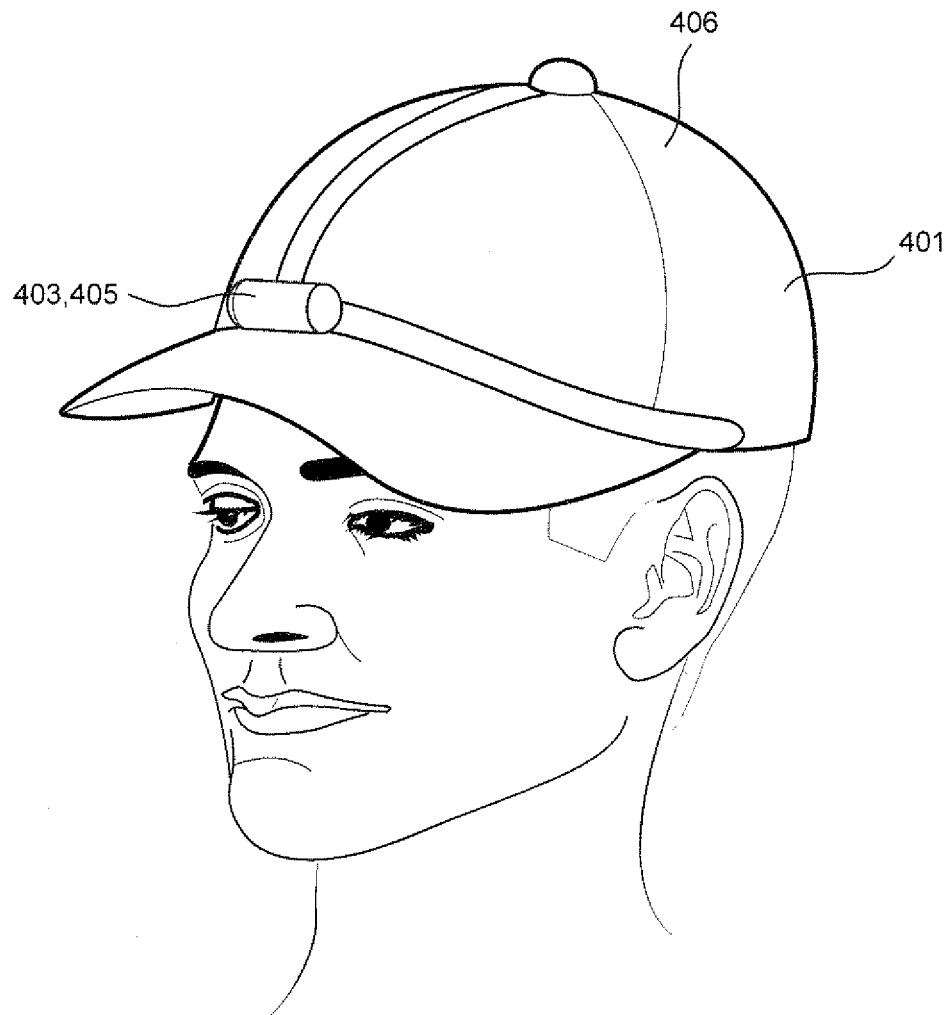
FIG. 4(a) is an illustration of an example of the present technology.
Figure 4B:
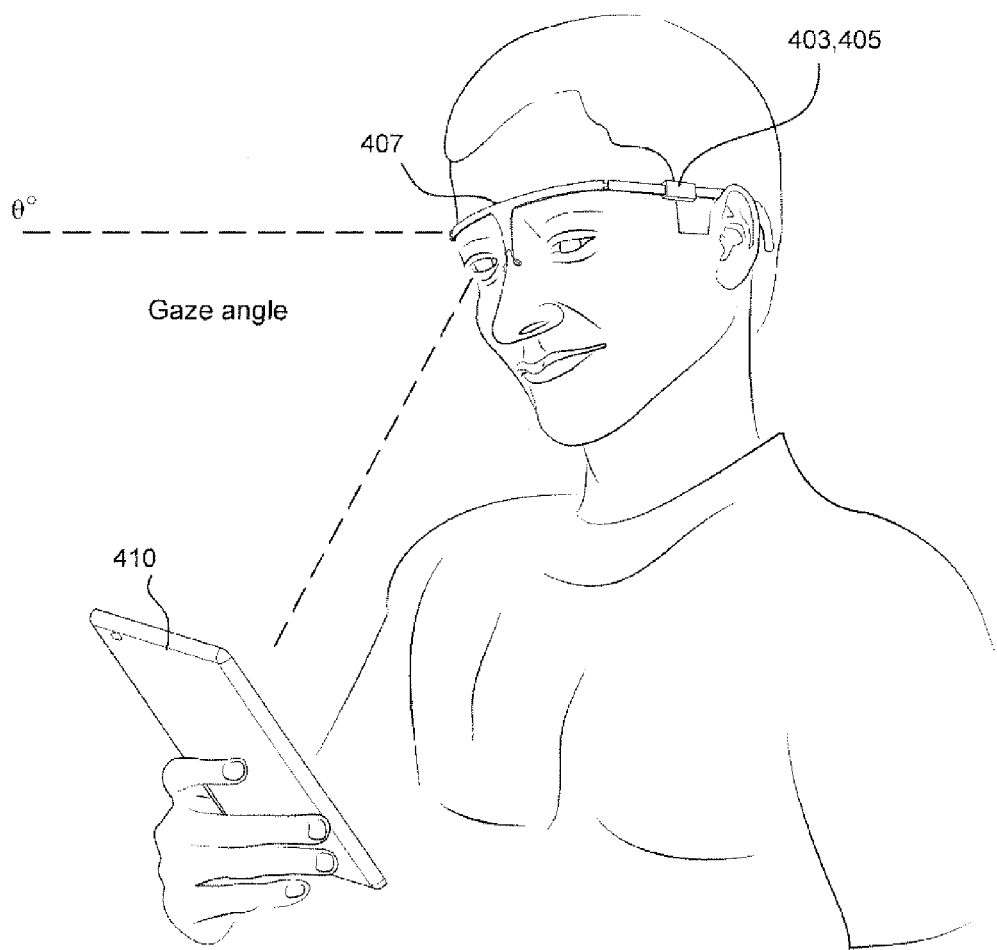
FIG. 4(b) is an illustration of another example of the present technology.
Figure 4C:
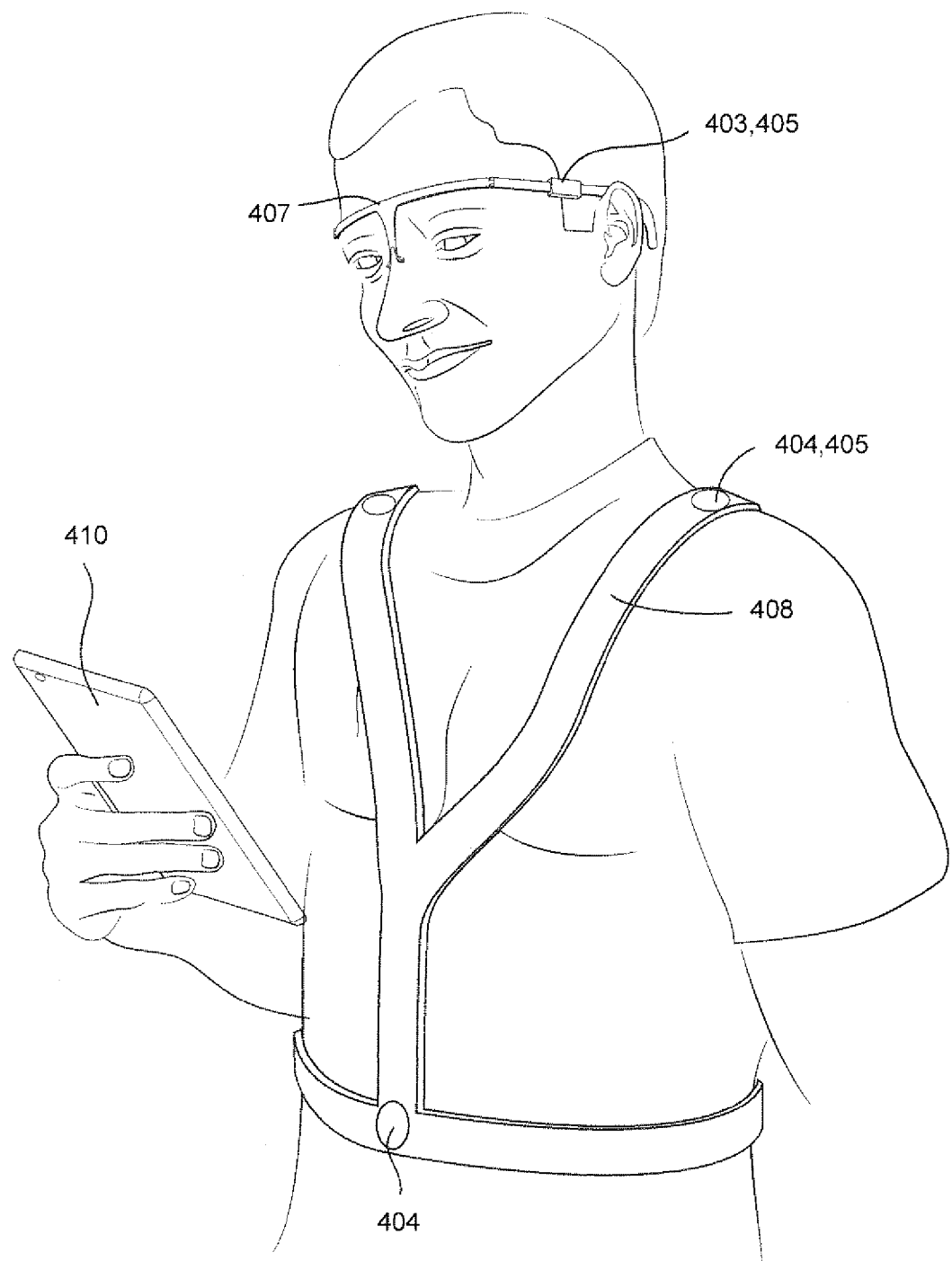
FIG. 4(c) is an illustration of another example of the present technology.

FIGS. 4(a)-4(d) demonstrate examples of the present technology. The wearable component 401 may be any item which can be worn by a user of a handheld electronic device 410 and accommodate one or more sensors 403, 404 necessary to monitor user posture and/or location relative to the handheld electronic device 410. The wearable component may include, for example, a hat 406, a set of glasses 407, a jacket 408, and/or any other wearable item which would be practically useful in measuring a user's posture, head or back position, direction of gaze, and other metrics for observing the posture of a user during use of a handheld electronic device. FIG. 4(a) illustrates such a device in the form of a ball cap or visor 406. FIG. 4(b) illustrates such a device in the form of lens-less glasses 407 which may be worn while using a handheld electronic device. The sensors described herein may also be incorporated into prescription or leisure glasses with lenses. FIG. 4(c) illustrates such a device in the form of a vest or jacket 408. With the vest or jacket aspect of the technology, a method of use may include a device worn on or about the head in addition to the vest or jacket to provide adequate data during use.

Each example is fitted with a control unit 405, which may include or be in communication with one or more sensors, a processor, a transmitter, a receiver, a transceiver, and/or an actuator capable of emitting light, sound, vibration, a change in temperature, and/or the like. The control unit 405 may co-exist within a housing with sensors 403, 404 or may be a separate element. The control unit may be located on a wearable component or within or attached to an electronic device.

The control unit and/or processor receives information from a selected sensor or set of sensors, analyzes the information received from the sensor, and then sends an action message to a device on the wearable component, and/or sends an action signal to the electronic device. The control unit may have the functionality to provide a progressive feedback system. For example, a first action message may be sent to a device on the wearable component like a light emitting diode or vibration actuator. If the user fails to respond to a first warning communicated to the user, the control unit may then send progressive warnings. For instance a second action message may then be sent to the electronic device to alter its operational state.

Figure 4D:
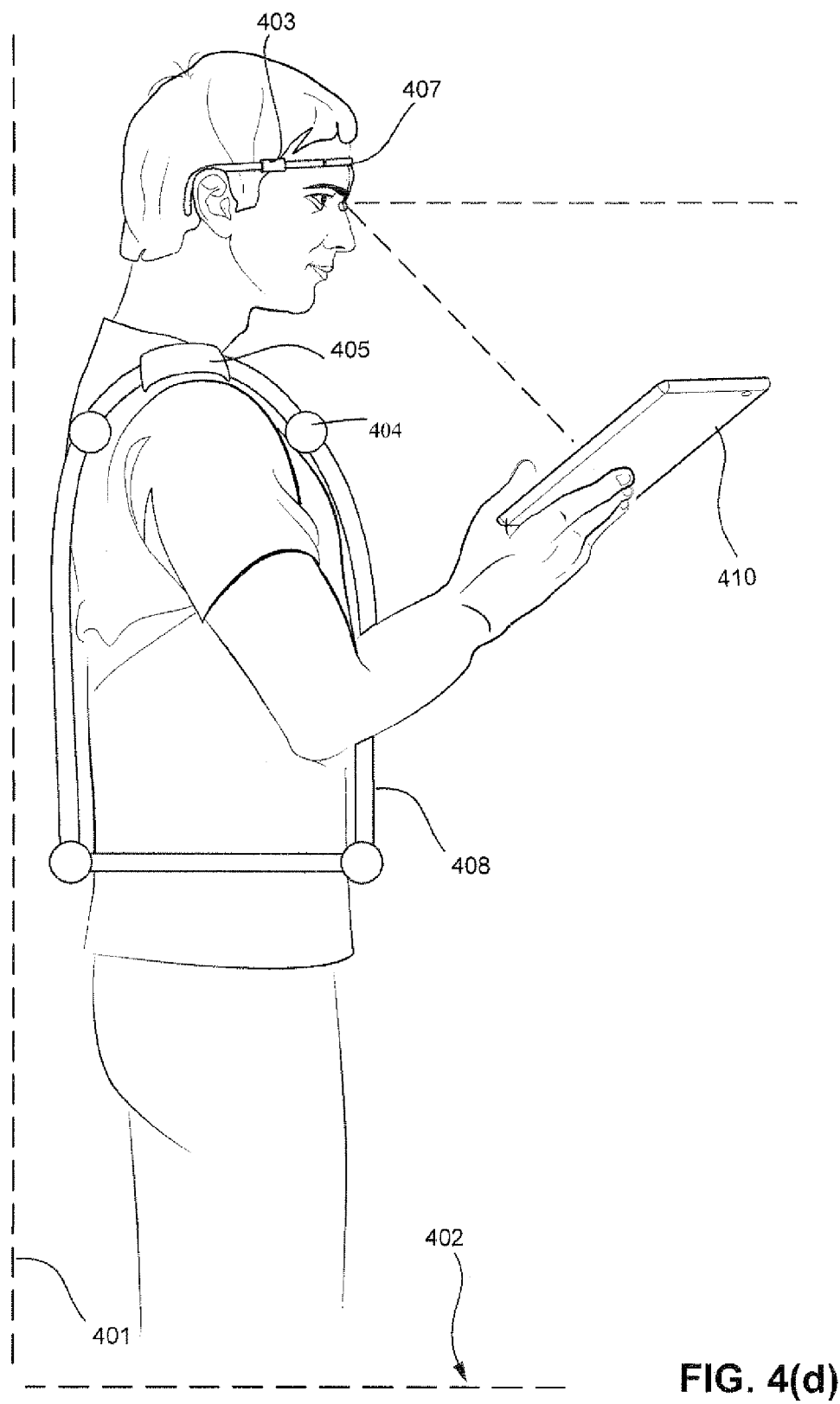
FIG. 4(d) is an additional illustration of an aspect of the example illustrated in FIG. 4(c).

FIG. 4(d) is an illustration of vest 408 being worn in a correct posture situation. Compare FIG. 4(d) with FIG. 1. Vest 408 and its corresponding sensor system 404 may monitor posture separately as well as in coordination with a wearable component 407 associated with the user's head. The vest 408 component may provide information and monitoring related to the torso, while the head-associated wearable component may provide information and monitoring for the head and neck.

3.1 System Configuration.

Figure 5:
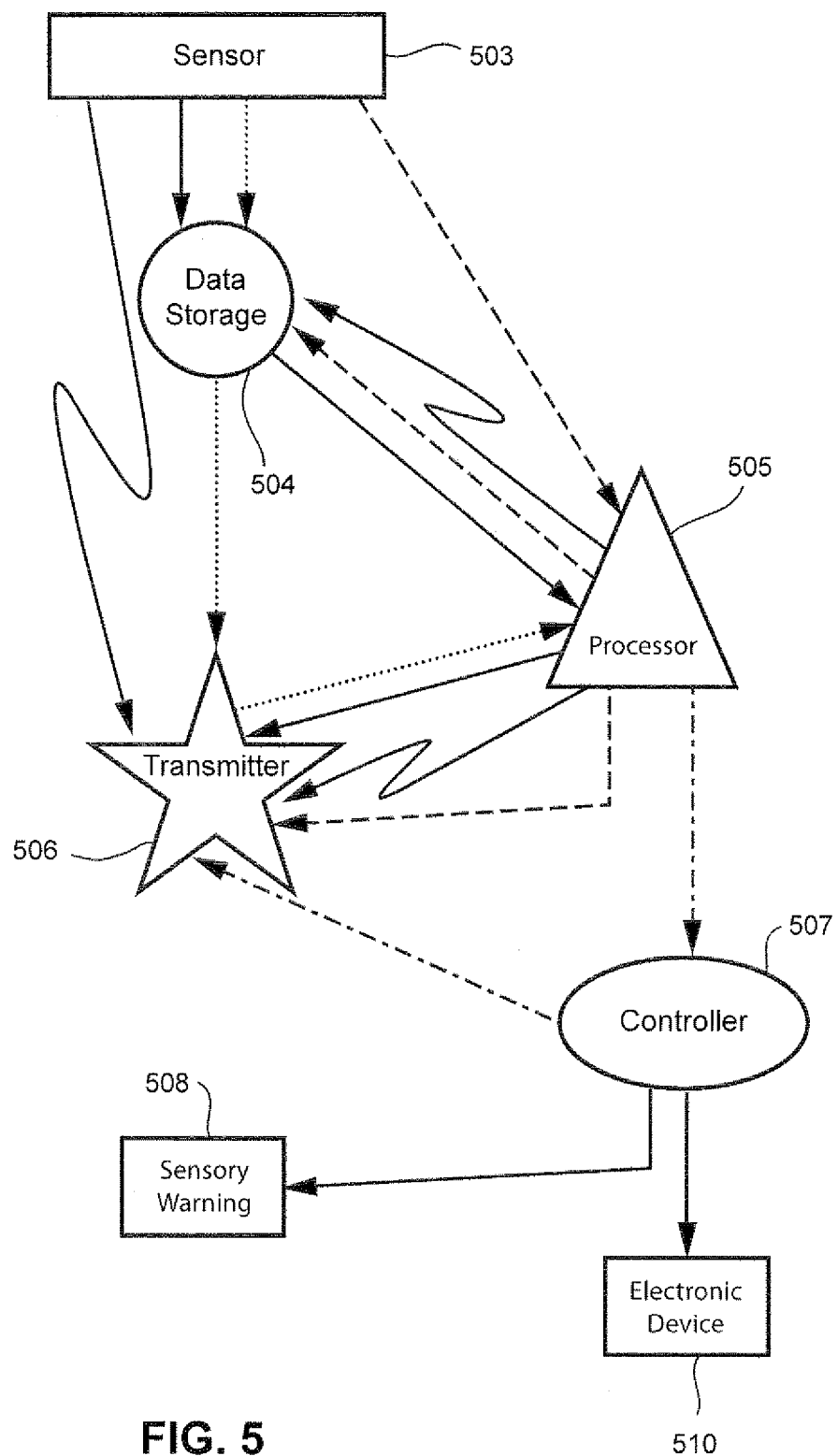
FIG. 5 is a system chart illustrating exemplary systems utilized by the present technology.

FIG. 5 is an exemplary illustration of the system utilized by the present technology. In particular, the system may rely on one or more sensors 503, which as previously discussed may measure posture-related metrics observable during use of a hand-held electronic device. The sensors may then, optionally, be connected directly or wirelessly at least to one of a data storage unit 504, a processor 505, and/or a transmitter 506. Depending on the configuration utilized in a particular embodiment, data measured by the sensors may be sent to the transmitter 506 which may, in turn, send the data to an external system featuring processor 505 and optionally, data storage unit 504, e.g. the electronic device 510 being used by the user may include a data storage device satisfactory for use as data storage unit 504. In another embodiment, the data is stored and/or analyzed directly by components located on the wearable component featuring the sensor 503 before being sent to the external electronic device 510 being used by the user. Regardless of the path the data takes, it may ultimately begin with sensor 503, pass through processor 505 and transmitter 506, and sent ultimately to controller 507, which is configured to signal the activation of any of a number of warnings 508 or alterations to the electronic device 510 being used by a user. The data may optionally also be stored in a separate data storage unit 504 configured to be accessible concurrently or at a later time for further data analysis.

The data may also be sent via a service such as electronic mail, to be read and further analyzed by, e.g., the parents of a child using the system as disclosed. Data collected and sent to be recorded and/or analyzed may include: time of use of the electronic device, the number of warnings issued by the system, the number of changes to the functionality of the electronic device were utilized by the system, and/or a registry of what activities, programs, and/or games were being viewed on the electronic device during use. The system which records and sends the data may also automatically prepare graphical representations of the data along with or independently of the data itself, such as graphs and charts, which may be time-based or cumulative.

Further, an application ("app") may be written and provided to the electronic device which works with the system to accomplish the goals described herein. Such an application, e.g. a "posture app," may be configured to receive data from the sensors directly or from the processor or control unit. The application may be written to interfere with the normal operation of the electronic device in response to control or action signals sent by the processor or control unit. The application may also or instead be written to record data and/or generate reports and communications concerning the data as described above.

The posture app may be written in such a way that a user of the electronic device may be able to install the posture app manually and locally or by downloading the application to the electronic device from a remote source. Upon installation of the posture app, the user and/or supervisors of the user, e.g., parents, may be prompted to select which other functionalities and applications may activate monitoring by the posture app. For instance, a user or the user's guardians may be provided with a list of the installed applications already on the electronic device and be presented with the option of marking empty checkboxes to indicate a preference for monitoring user activity related to a particular installed application. In another instance, the prompting functionality of the posture app may be designed to allow a user or the user's supervisor to indicate specific websites, e.g., on the internet, which may activate monitoring by the posture app. Examples of such websites include Youtube.com, Facebook.com, and the like. Such indication, like the marking of checkboxes, may be performed using a touchscreen, a stylus, a movable cursor controlled locally or remotely, or any other method for interacting with the electronic device. Subsequent installations of additional applications or updates to software on the electronic device may trigger a subsequent prompt regarding the newly installed applications/software and/or all installed applications/software.

Using the installation prompt discussed above, a user and/or supervisors/guardians of the user may provide selective enablement of the posture monitoring system discussed herein as an optional design feature.

The application may provide a prompt for a user and/or a guardian or supervisor of a user to verify their identity and permission to make changes to settings within the app. The user and/or guardian may be asked to input a password to have access to a configuration page. The configuration page may allow a user or guardian to log in, change a password, set a time allowance for playing which may be in terms of available minutes or a specific time, window within which the user may use the device, and also to select which programs are available and which are unavailable. For example, the program may utilize color changes to indicate available (e.g., green) programs versus unavailable (e.g., white) programs. After the user and/or guardian or supervisor of the user log out of the configuration system, the user of the system lacking a password to access the configuration page will only be able to access "available" programs. On the user page, there may be a separate indicator communicating to the user that a particular available program requires use of the wearable posture monitoring system, while some available programs may be set to be available without requiring the use of the wearable posture monitoring system. For instance, if a user selected an icon for an available program, there may be a status indicator displayed somewhere on the screen in addition to the icons for the available programs. The status indicator would be able to change between "required" (e.g., red) and "not required" (e.g., green) indicators to inform the user whether the wearable posture monitoring system is required to activate and use the particular program.

Once a user or the user's supervisor has installed the posture app and selected which features and/or programs are to be monitored by the posture app, any time the user of the electronic device attempts to begin using the electronic device to access one of the selected features and/or programs, the posture app may provide a notice to user to put on a wearable component and/or ask for confirmation that a wearable component of the posture monitoring system is being worn. During use, the system monitors the wearable component for minor movements which are expected during use and while being worn to ensure the wearable component is being properly utilized during use of the electronic device. However, at the beginning of use of the pre-selected features and/or programs for monitoring, a delay time may be utilized to allow the user time to put on the wearable component before monitoring for confirmation that the wearable component is being worn. A delay time may also and/or instead be utilized prior to the system monitoring posture generally to give the user time to begin use of the electronic device and establish a position of use.

3.2 Warning System

The wearable component may be provided with the ability to warn the user of poor posture through a variety of warning systems. For example, the wearable component comprises devices which may emit visual, auditory, and/or tactile warnings such as lights, sounds, and/or vibrations, to indicate to the user their current state of being in a position with poor posture. Such devices may include but are not limited to lights such as LEDs, speakers, servo motors. Such warning devices may be incorporated into the and onto the wearable component. Additionally, the wearable component may be provided with the ability to communicate directly with the electronic device, either directly to the handheld aspect or to the electronic device itself, if the handheld component is separate from a base unit with which the handheld component associates. Such communication ability is provided by the control unit 405 and associated components described above, including a transmitter and/or data storage device.

3.3 Communication Between Posture-Monitoring and Electronic Device

The connection between the wearable component and the electronic device may be wired, but is preferably accomplished wirelessly. To create such a connection, infrared, radio, or other wireless signals and associated devices for transmitting and receiving such signals may be used. The connection between the wearable component and the electronic device and/or its handheld component may be established using a BlueTooth™ connection or a Wi-Fi connection or the like.

The wearable device may be fitted with a processor to analyze the information being collected by the various posture and/or location sensor(s) provided on the wearable component. The wearable device may also be fitted with a storage unit configured to record any data collected by the various sensors provided on the wearable component. Such collected data may be accessible directly or wirelessly via the storage unit. The storage unit may be a physical device or the data collected may be sent to a "cloud" or other server system.

The wearable component may also omit a processor and storage unit and instead be configured to directly transmit the sensor readings to the electronic device.

The electronic device and/or its handheld component may likewise be provided with devices to provide warnings concerning poor posture which may be activated by the wearable component and its sensors.

The wearable component may be configured to access and interact with a corresponding program installed on the electronic device. The remote program on the electronic device may be configured to respond to signals from the wearable component and its sensors; a response by the electronic device may activate an alarming device of the type discussed above.

The wearable component may be configured to access and interact with an external device to monitor and/or record data measured by the sensor(s). Such an external device may be connected to the wearable component through any of the previously discussed communications means, including wireless local area networks (WLAN) and Wi-Fi.

Additionally, the electronic device may be configured to alter its performance in response to the information collected by the wearable component and analyzed by either the wearable component or by the associated program found on the electronic device. Such an alteration may be presented to the user in the form of a visual warning, including a text warning over any image on an associated screen or a change in the color, resolution, size, orientation, or arrangement of the image on the associated screen.

3.4 Progressive Feedback

The warning provided to the user by either the wearable component or the electronic device may be configured to escalate in intensity if the user fails to respond to the warning when issued. The warning system is ideally configured in a feedback loop. The user is warned about poor posture and if the user is responsive and the posture is corrected, the warnings cease and the electronic device continues working normally. However, if the user is warned about poor posture and fails to correct the poor posture, the system utilizes a counter to remember that a first warning was previously provided (e.g., within a certain, predetermined amount of time or within a certain, predetermined range of values as observed by the associated sensors) and moves on to a second level warning. If second level warnings are likewise ignored, the system may escalate to third and additional level warnings until the user responds to correct his or her posture. The second level warnings may become more intense: brighter, louder, or using increased frequency of vibration, or in the case of the electronic device altering its output, the device may cause its screen to dim, change color, orientation, arrangement of pixels, or the like, or shut down altogether if one or more warnings are given and ignored.

The system is designed to utilize positive and/or negative reinforcement. For example, guardians of a child may choose a playing time or duration through the application. If the guardian chose, for example, 120 minutes of playing time for the user:

a. Positive Reinforcement (Reward): If the user has less than a predetermined number of warnings, W, during the first X, e.g., 60, minutes of playing time, the system may be programmed to increase the playing time by a given amount or percentage, e.g., 25%. In this example, the user would receive a bonus of 30 minutes (for a total playing time of 150 minutes) for exhibiting good posture during use.

b. Negative Reinforcement (Punishment): If the user has more than a predetermined number of warnings, W, during the first X, e.g., 60, minutes of playing time, the system may be programmed to decrease the playing time by a given amount or percentage, e.g., 25%. In this example, the user would receive a penalty of 30 minutes (for a totally playing time of 90 minutes) for exhibiting poor posture during use.

4. Failure to Properly Utilize the Wearable Component

Figure 6:
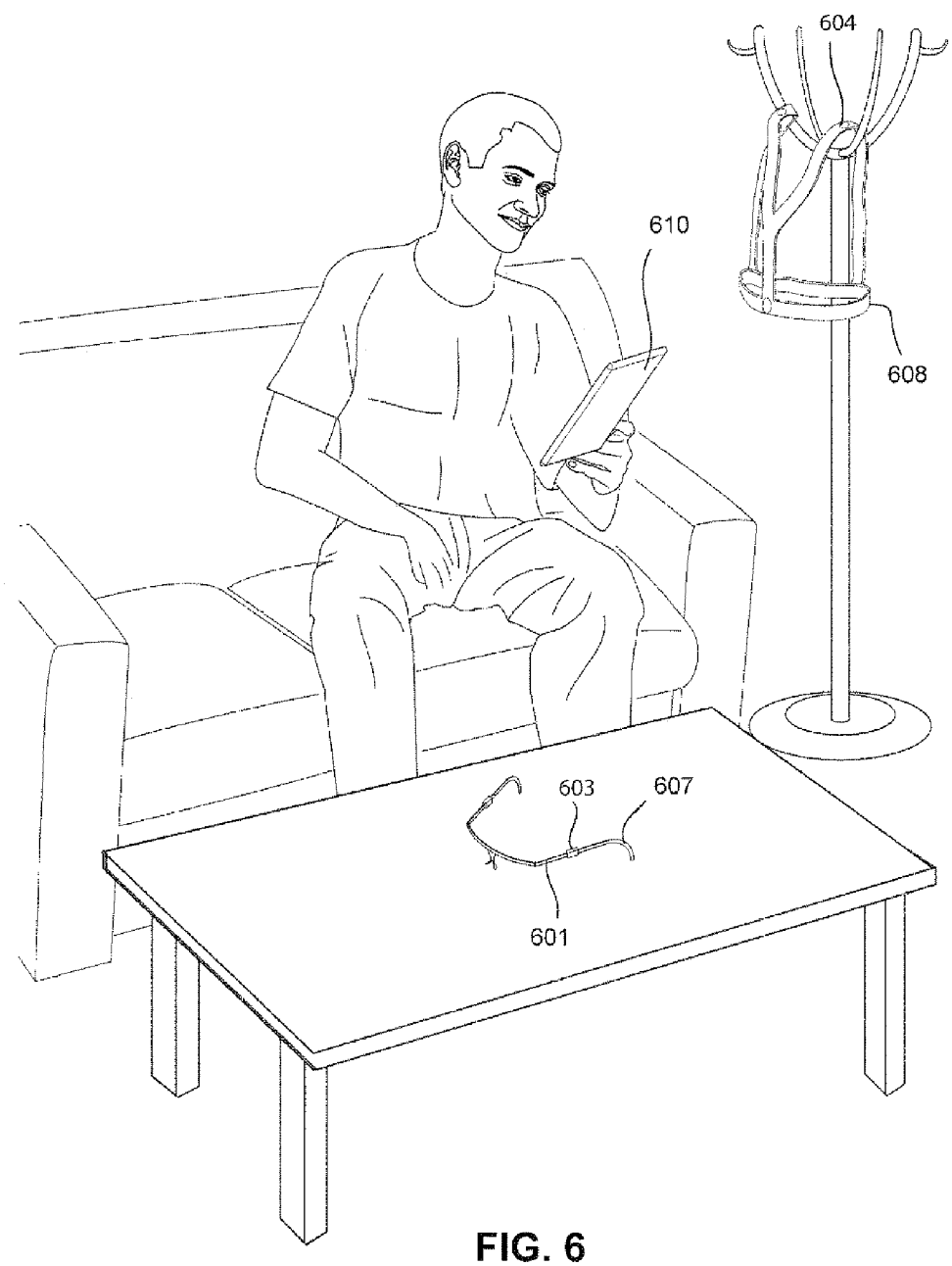
FIG. 6 is an illustration of an additional aspect of the examples illustrated in FIGS. 4(a)-(d).

FIG. 6 illustrates another aspect of the present technology includes a device to notify the system if the user is not wearing the wearable component. Regardless of which sensor is used to monitor posture (tilt, etc.), a person wearing such a sensor, especially if the person is a youth, is expected to move enough to cause at least some change in the variable observed by the sensor. For example, if the system monitors the tilt angle of the head, with an angle measurement of zero degrees being considered "normal" (a person looking straight forward), a user could simply place the wearable component 601 on a table or other flat surface such that the sensor would detect a zero degree tilt to attempt to fool the system and avoid the warnings. However, with the use monitoring system aspect, the system may also expect some at least minor variation in the readings taken by the sensor, which is indicative of use since a person wearing the device during use of electronic device 610 may likely be moving at least minimally during use. A lack of movement and use by the system can likewise trigger warnings similar to those discussed above for poor posture. Normally, the head moves regularly due to normal blood flow, whereby each heart beat may cause the head to move slightly (as little as less than a degree) due to the jet of blood flowing through the carotid artery with each heartbeat.

In addition to the above features, the system described may also utilize a proximity sensor which determines a distance between the wearable component and the handheld component of the electronic device. The use of such proximity detection is an additional step to ensure that the user is using the wearable component, as well as serving as an additional tool to aid in reducing poor posture configurations involving holding the handheld component of the electronic device at various locations relative to the user.

5. System Logic

Figure 7:
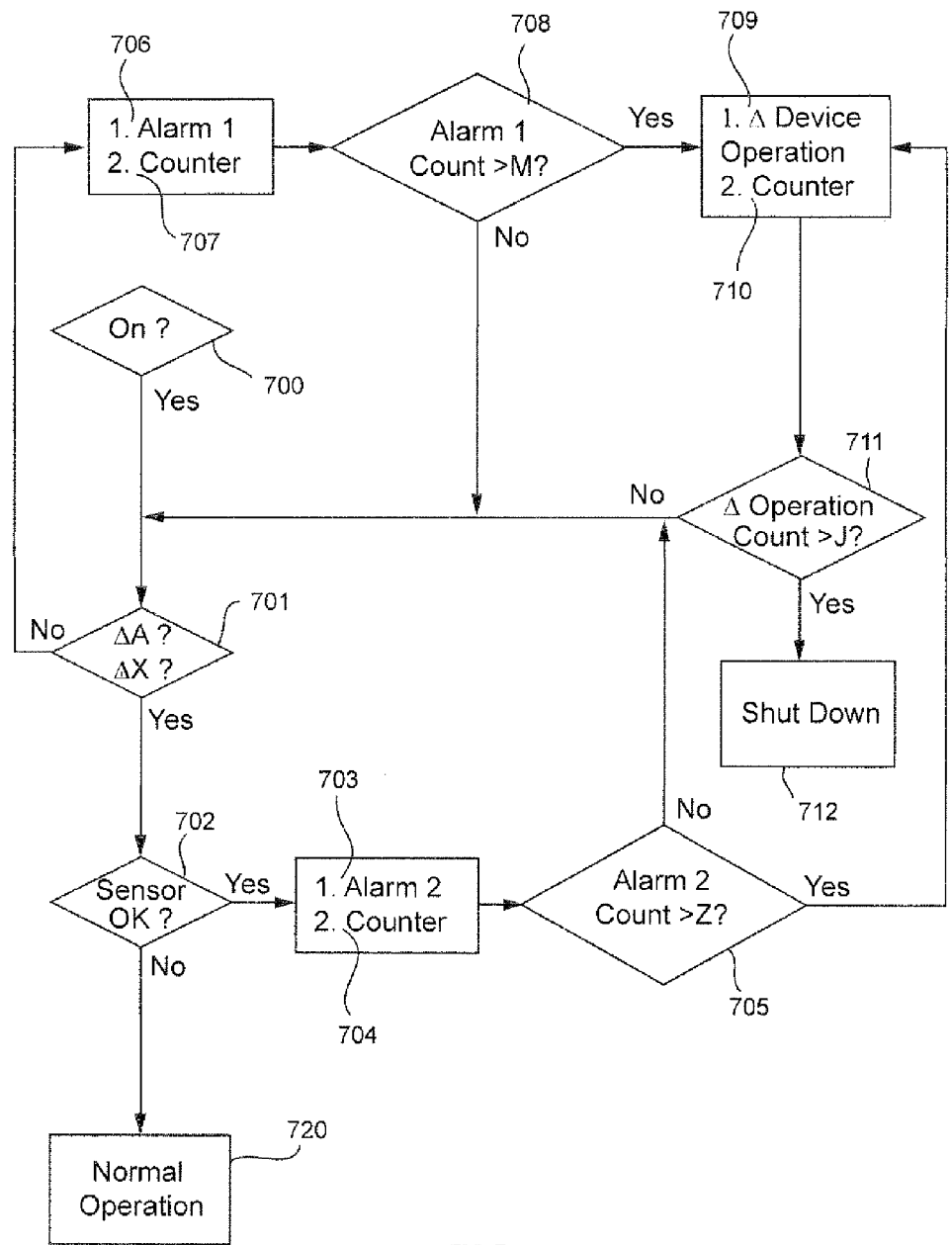
FIG. 7 is a flow chart illustrating exemplary functioning of the present technology.

FIG. 7 illustrates a general flowchart for this system. The steps for this system to function are at least (1) check for the system power being "on," (2) check the system for minor movements based on the sensor chosen to indicate the wearable component is being worn/used, and (3) checking the monitored condition for compliance with a predetermined threshold, e.g., a tilt angle within a given degree range measurement. If the system is on 700, the system may check to see if the user is actually wearing the wearable component via sensors designed to detect minimal movements 701. For instance, sensors may detect minimal lateral movements, $\Delta X$, and minimal angular movements, $\Delta A$. If no movements are detected, indicating the wearable component is not being worn, an alarm or warning may be triggered 706, either via the wearable component or the electronic device. Then, in conjunction with the sounding of alarm 706, a counter may increase the value of a wearing component monitor value 707 stored in a control unit associated with either the wearable component or the electronic device.

The system may then check to see if counter 707 has at least reached a predetermined value, M, in step 708. If the alarm counter 707 has at least reached M, the system then may result, in a change to the operation of the electronic device 709 and an increase of in device operation counter 710. A change in the operation of the device may include altering, freezing, or blacking out the screen or a section thereof for a predetermined period of time. The system then checks counter 710 to see if counter 710 has at least reached a predetermined value, J, in step 711. If the counter 710 has at least reached J, the system may cause the electronic device to power down. In the alternative, the device may continue indefinitely within a loop providing changes in operation to the device of increasing severity and/or length of time for interference with normal operation if the user does not correct his/her posture.

It on the other hand, counter 707 has not at least reached M in step 708, the system may then monitor the device for movement again after a predetermined amount of time. If movement is again not detected, another warning or alarm may be triggered, which may or may not be different from the first alarm or warning activated, and the counter for the wearing component monitor value may again be increased. This cycle may repeat until either movement is detected in step 702 or enough warnings are issued that the wearing component monitor value exceeds a predetermined value, M, in step 708 and the device operation counter 710 also exceeds a predetermined value, J, in step 711 and instead of a warning, a signal to shut down the electronic device may be sent by the system 712.

If the system detects the minor movements associated with a user correctly wearing the wearable component in step 701, the system then consults the sensor in step 702 chosen in a particular example to assess if the user is exhibiting correct posture, based on a given sensor. For example, if the sensor is a tilt sensor installed on the wearable component to provide data approximating the angle of gaze of the user, the sensor in step 702 may monitor the tilt angle of the wearable device corresponding to the angle of gaze of the user. Such a tilt sensor may monitor at least two axes of a reference plane for tilting. A tilt sensor may also be supplied which is able to measure full motion in at least three axes and may comprise additional sensors functioning as a system. A tilt sensor may also comprise an accelerometer.

For example, the wearable component may be a frame similar to that provided for eyeglasses. Such a frame can be provided either with or without lenses, as the user desires. In this example, the frame is fitted with a sensor. Such a sensor may measure a tilt angle from the horizontal axis. The system compares the information about, e.g., tilt, collected by the sensor with a predetermined acceptable, e.g., tilt angle value. Examples of such tilt sensors include, but are not limited to, mercury switches, tilt switches, rolling ball sensors, and various other tiltmeters and inclinometers. If the observed value falls within a predetermined acceptable range for the observed sensor value, in this case, a tilt angle from zero to thirty degrees below horizontal, the system continues to operate the electronic device as normal. However, if the observed value falls outside the predetermined acceptable range for the observed sensor value, e.g., a tilt angle greater than a predetermined maximum deflection down from horizontal, the system follows a similar feedback loop of issuing warnings or alarms to the path described above.

If the observed value of the sensor in step 702 is not within a predetermined range, warning or alarm 703 is initiated, which may change upon subsequent or repeat warnings, and increasing an unacceptable sensor value counter 704. The value of counter 704 is then compared to a predetermined value, Z, in step 705. If the value of counter 705 has reached at least Z in step 705, as an additional step, additional warnings may be given in the form of changes to the operation of the electronic device 709. As before, a counter 710 is increased and compared with device operation counter 710. If the counter 710 has reached at least predetermined value, J, the system may initiate a shutdown.

This cycle may repeat until either the user of the electronic device wearing the wearable component corrects their posture, as indicated by signals demonstrating correctly wearing the device in step 701 and sensor measurements being within a predetermined range in step 702 (signaling normal operation 720 to the electronic device), or until the unacceptable sensor value counter has reached a predetermined counter number 705 and the device operation counter 710 has reached a predetermined number, at which point, the electronic device may be signaled to shut down.

Figure 8A:
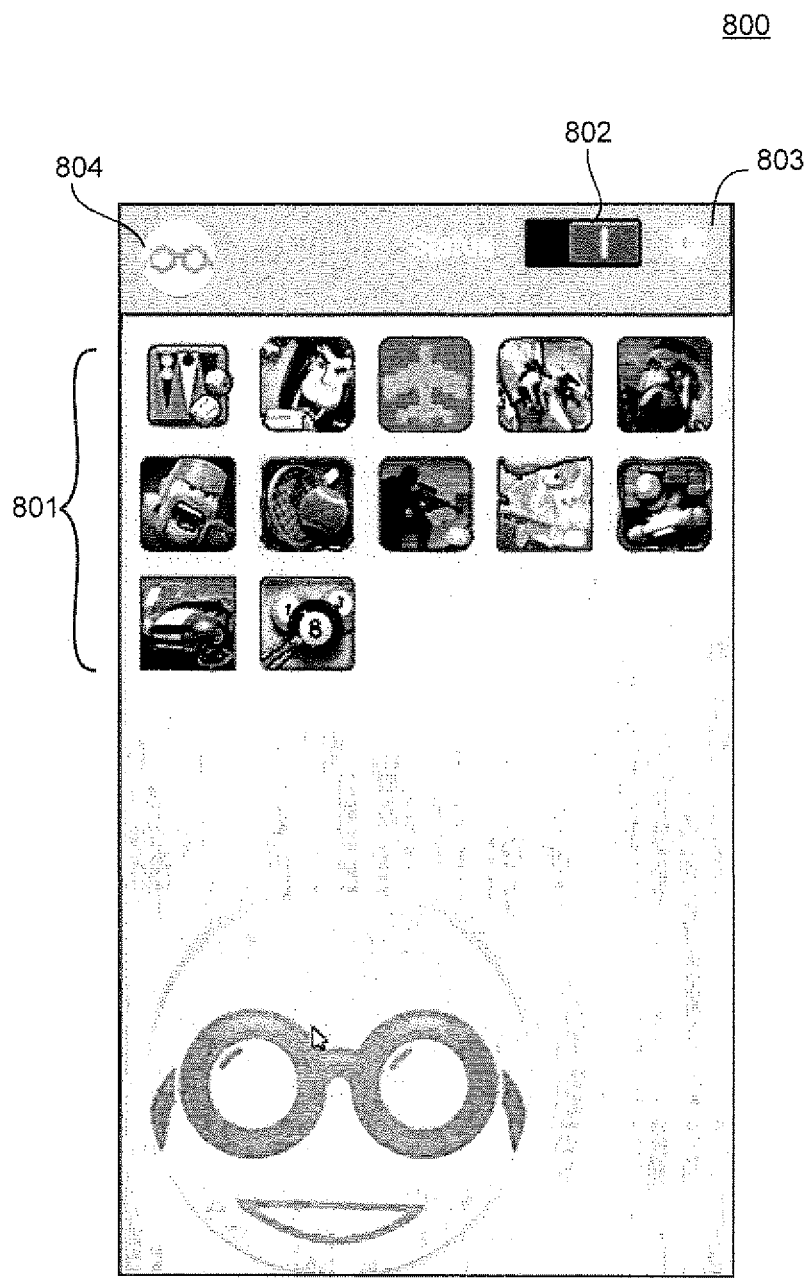
FIG. 8(a) is an exemplary illustration of an application page available to a user of the application associated with the present technology.
Figure 8B:
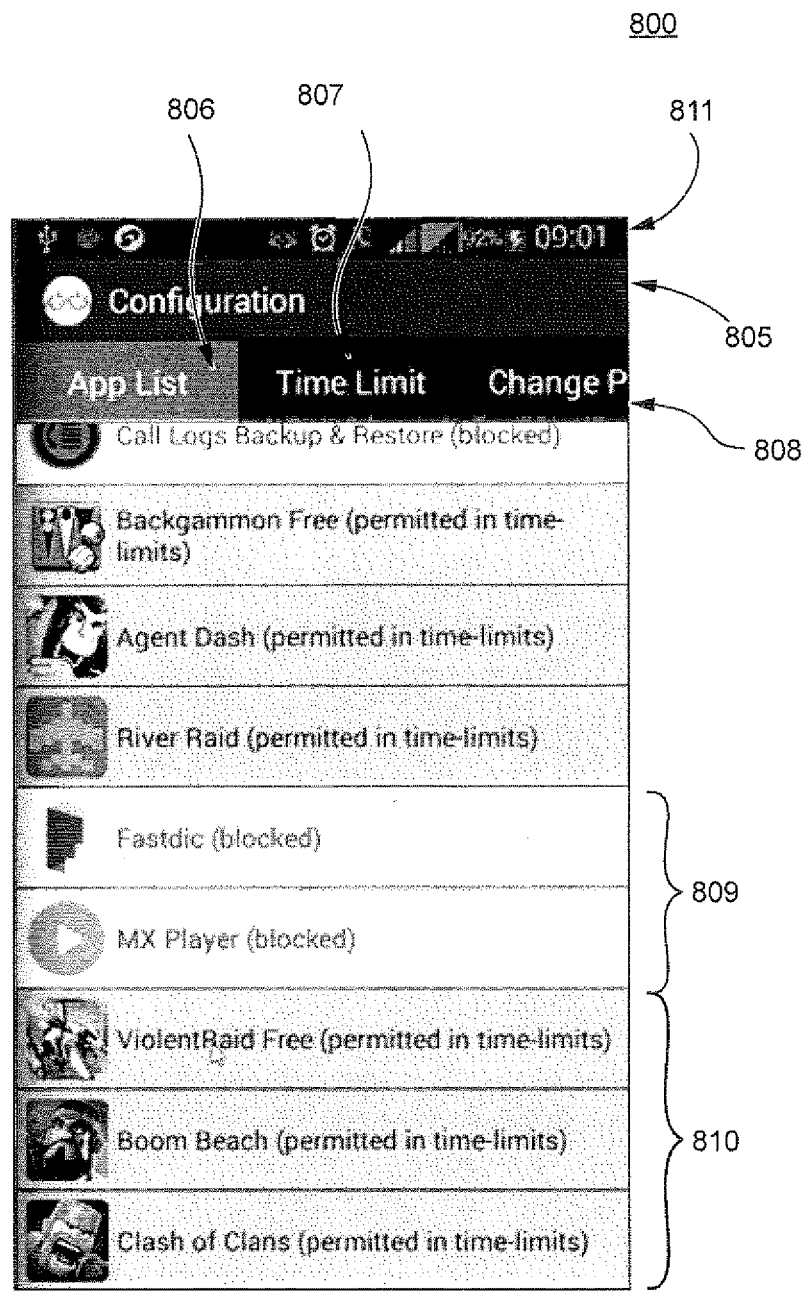
FIG. 8(b) is an exemplary illustration of an application configuration page available to a user of the application associated with the present technology.

FIGS. 8(a), 8(b) are a set of exemplary images of screens which may be visible to a user as presented by the application. FIG. 8(a) illustrates an example of an application page 800 available to a user of the application and wearable posture monitoring system after the application has been configured by a supervisor or guardian with access permissions (e.g., a password). As is visible in the illustration, the user is presented with a list or display of available programs 801 which the user may select. The user is also presented with a status indicator 802 which, upon selection of one of the available programs, indicates to the user whether the selected program requires or does not require use of the wearable posture monitoring system for use. Additionally, there may be provided a settings icon 803 which may be programmed to access a log in and/or configuration page or other settings not visible on the application page in FIG. 8(a). The user page may also feature an icon for the program 804, which may be programmed to illustrate how to wear and/or use the wearable posture monitoring system. The program icon 804 may also or instead be programmed to illustrate a reflection of the current position of the wearable posture monitoring system, such as (1) not on the user, (2) on the user correctly and/or in a good posture position, or (3) on the user incorrectly and/or in a bad posture position.

FIG. 8(b) illustrates an example of an application page available to a user and/or guardian or supervisor in possession of a password or other access code to the configuration page 805, as clearly identified at the top of the page. The user and/or guardian or supervisor may be presented with a separate password log in page or merely a pop-up requesting a password or other access method, which may include emerging technology including retinal scanners, thumb or fingerprint scanners, or other biometric devices which may be utilized with such electronic devices. The configuration page 805 illustrated in FIG. 8(b) includes at least an application list 806, a time limit selector 807, and a change password option 808. Additional tabs within the scope of functions of this application may be added, these are exemplary. Time limit selector 807 may present the options including universal time limits for the use of any electronic device and/or programs within a predetermined time period, e.g., 60 minutes of use allowed per 6 hour period, or may alternatively allow the selection of different time limits for different programs on the electronic device. The change password option 808 may allow for a user with permissions to change the password to access the configuration page 805 as well as to activate or deactivate other security features such as biometric access tools. Below the tabs, the applications installed on the electronic device may be listed or otherwise displayed, with the currently blocked programs 809 being displayed in a first state or color (e.g., white) and currently available programs 810 being displayed in a second state or color (e.g., darkened). The configuration page may be programmed to continuous display the status of the electronic device 811 as well, illustrated in FIG. 8(b) as the upper bar of, e.g., a cellular telephone, with power supply, data transfer, alarm, and other iconic data supplied by the electronic device independently of the present technology.

Figure 9:
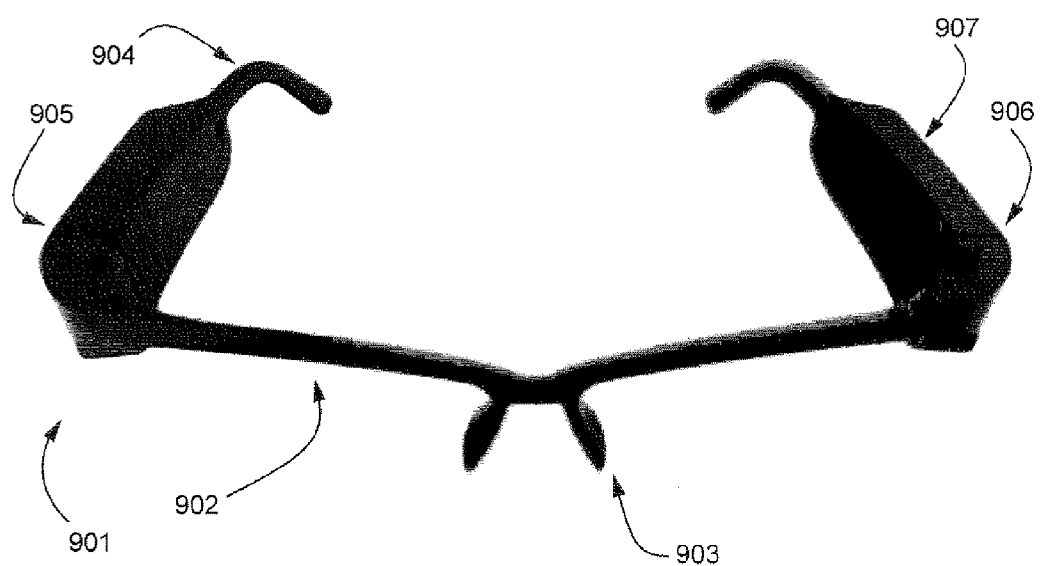
FIG. 9 is an exemplary illustration of an example of the present technology.

FIG. 9 is an illustration of one example of the present technology in the form of a wearable frame to be worn similar to a pair of reading glasses or sunglasses. The frame is worn during use of an associated electronic device which communicates with the frame and may utilize the application and programming described in FIGS. 8(a)-8(b). In FIG. 9, the example includes a wearable component 901 which includes a frame 902, a nose engagement device 903, an ear engagement device 904, a component housing 905, at least one sensor 906, illustrated within the component housing 905 in this example, and at least one control unit 907 also illustrated within the component housing 905 in this example. In alternative configurations, the sensor and/or control unit may be external to any housing on the device. The configuration illustrated in FIG. 9 may be known commercially as the "EyeForcer"™.

While the present technology has been described in connection with what are presently considered to be practical examples, it is to be understood that the present technology is not to be limited to the disclosed examples, but on the contrary, is intended to cover various modifications and equivalent arrangements included within the spirit and scope of the invention. Also, the various examples described above may be implemented in conjunction with other examples, e.g. aspects of another example to realize yet other embodiments. Further, each independent feature or component of any given assembly may constitute an additional example.

The invention claimed is:

1. A wearable posture monitoring system configured to monitor and provide feedback regarding a user's posture while operating and viewing a portable electronic device, the system comprising:
   a wearable component configured to be fit on or about a head of the user;
   a sensor mounted on the wearable component configured to monitor posture of the user based on at least a head position or head orientation of the user; and
   a transmitter configured to transmit data related to posture wirelessly from the sensor to a receiver on or in the portable electronic device;
   wherein:
   the data transmitted by the transmitter to the portable electronic device is configured for use as input by a computer executable application program to:
   provide progressive negative feedback regarding posture during use of the portable electronic device to the user based on data from the sensor, by generating a first signal that is configured to warn the user of abnormal or poor posture, and thereafter if the posture of the user fails to be corrected, by generating a second signal configured to alter the output provided to the user by the portable electronic device,
   provide positive reinforcement to the user via the portable electronic device if the user's posture is acceptable, based on the data transmitted from the transmitter, and
   generate for display a screen listing available programs, and identify available programs which require use of the wearable component to be executed.

2. The wearable posture monitoring system of claim 1, wherein the system is configured to continuously monitor the user's reaction to the feedback supplied to the user during use of the portable electronic device.

3. The wearable posture monitoring system of claim 1, wherein the feedback is provided in the form of auditory, visual, or tactile cues or the feedback is provided by causing the portable electronic device to display a warning message.

4. The wearable posture monitoring system of claim 1, wherein the sensor comprises a tilt sensor configured to monitor the gaze angle of the user during use of the portable electronic device.

5. The wearable posture monitoring system of claim 1, wherein the system is configured to allow the portable electronic device to operate for time in excess of a finite, predetermined amount of time in response to observed good posture.

6. The wearable posture monitoring system of claim 5, wherein the system is configured to prevent the portable electronic device from operating for the entirety of the finite, predetermined amount of time in response to observed poor posture.

7. The wearable posture monitoring system of claim 1, wherein the portable electronic device is a hand-held portable electronic device, and wherein the system is configured to monitor posture based on the head position or the head orientation of the user during use of the hand-held portable electronic device.

* * * * *